United States Patent [19]

Deschamps et al.

[11] Patent Number: 5,674,265
[45] Date of Patent: Oct. 7, 1997

[54] APPARATUS AND METHODS FOR COMMUNICATIONS WITH IMPLANTED ACTIVE MEDICAL DEVICES

[75] Inventors: Herve Deschamps, Suresnes; Chikyam Lee, Arcueil, both of France

[73] Assignee: ELA Medical S.A., Montrouge, France

[21] Appl. No.: 363,742

[22] Filed: Dec. 23, 1994

[30] Foreign Application Priority Data

Dec. 31, 1993 [FR] France ................... 93 15940

[51] Int. Cl.⁶ ........................................ A61N 1/00
[52] U.S. Cl. .................. 607/60; 607/32; 128/901; 128/903; 340/41; 455/138; 455/232.1
[58] Field of Search ..................... 607/9, 30–32, 607/52, 59, 60; 128/696, 697, 901–903, 653.1; 364/413.26; 455/137, 138, 234.1, 246.1, 296; 340/870.04, 870.05, 870.41

[56] References Cited

U.S. PATENT DOCUMENTS

| | | | |
|---|---|---|---|
| 3,262,057 | 7/1966 | Miller et al. | 455/138 |
| 3,555,529 | 1/1971 | Brown et al. | 455/137 |
| 4,284,856 | 8/1981 | Hochmair et al. | |
| 4,357,497 | 11/1982 | Hochmair et al. | |
| 4,531,523 | 7/1985 | Anderson | 607/32 |
| 4,944,299 | 7/1990 | Silvian . | |
| 5,069,210 | 12/1991 | Jeutter . | |
| 5,168,871 | 12/1992 | Grevious | 128/903 X |

FOREIGN PATENT DOCUMENTS 2 465 474   3/1981   France .

*Primary Examiner*—Jeffrey R. Jastrzab
*Attorney, Agent, or Firm*—Orrick, Herrington, & Sutcliffe, LLP

[57] ABSTRACT

Process and apparatus for extracting a useful signal emitted by an implanted active medical device in the presence of parasitic signals. This device includes a plurality of signal receivers located at distinct points. The signal receivers are sensitive to the magnetic component of the electromagnetic signals and separated from each other by a distance that is negligible as compared to the wavelength of the electromagnetic signal. A plurality of amplifiers are provided with one amplifier being associated with each signal receiver and each amplifier having an adjustable gain. The amplified signals are summed by an adder, and the summed signal (V(t)) is evaluated using a magnitude (|V|) representative of the level of the summed signal. A processing means is used in the absence of the useful signal to adjust the gain of each amplifier, as appropriate, to minimize the magnitude in a preliminary step, and to maintain the amplifier gains at the adjusted values in a subsequent step, in the presence of the useful signal. As a result, the useful signal is acquired and the perturbing signals are suppressed.

21 Claims, 1 Drawing Sheet

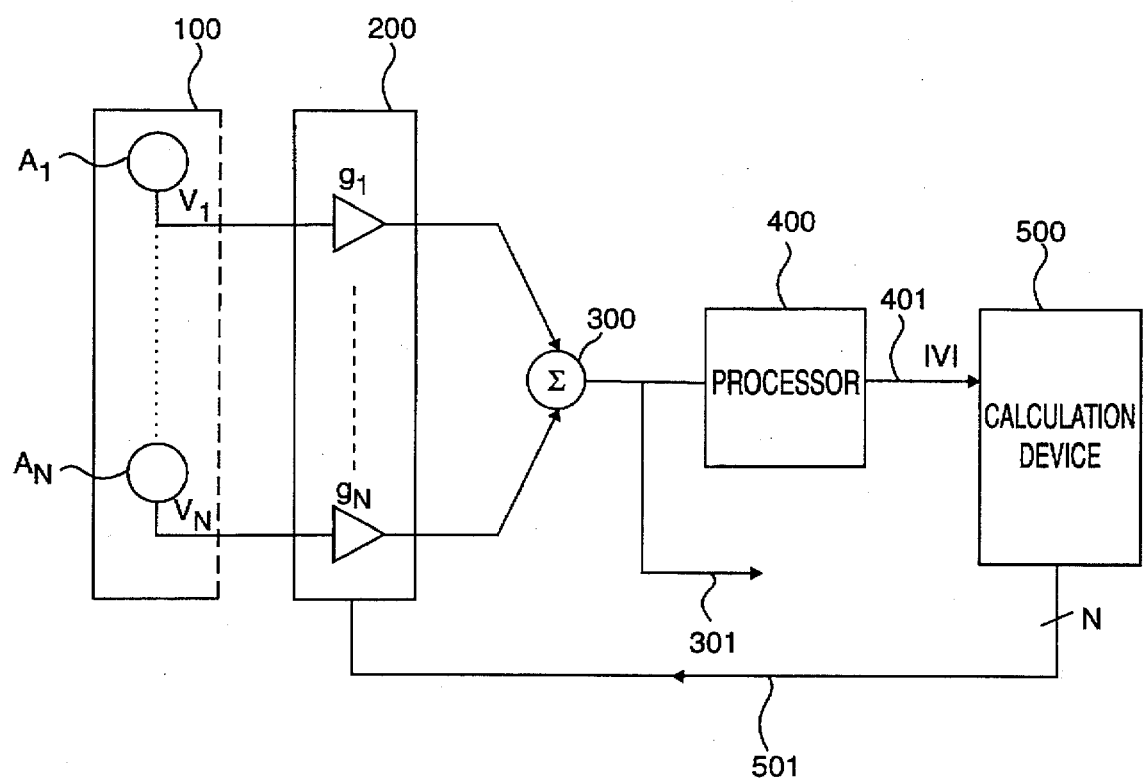

APPARATUS AND METHODS FOR COMMUNICATIONS WITH IMPLANTED ACTIVE MEDICAL DEVICES

FIELD OF THE INVENTION

The present invention concerns the area of active implanted medical devices, and more particularly the sensing of signals emitted during communication transmissions between the implanted device and an external control device.

BACKGROUND OF THE INVENTION

Active implanted medical devices include, among other devices, cardiac stimulators (pacemakers), cardiac defibrillators, neurological stimulators, muscle stimulators, medication pumps (e.g., insulin pumps), and cochlear implants. Such devices are generally referred to herein as an "implant".

These devices, once implanted, are typically programmed using an exterior control device called a "programmer". The programming typically includes the transmission of operating parameters, software instructions, and other information to the implant, and responsive transmissions from the implant to the programmer. The latter typically include, but are not limited to, the verification of the implant operating parameters (including programmed parameters and preset or fixed parameters), and the transmission of information that has been recorded by the implant. These transmissions occur by an electromagnetic signal transmission which is called "telemetry" in the technique in question.

The external programmer is supplied with a telemetry receiver that is placed in proximity to the implant site. The receiver element typically includes an antenna to receive the telemetry signals, more typically a coil that captures the magnetic field of the electromagnetic signal emitted by the implant.

Such a receiver coil is typically formed of about 40 windings of wire, wound around a spool surface of approximately 25 cm$^2$. This coil collects a useful signal comprised of between 10 µV and 1000 µV, depending on the distance between the receiver coil and the implant transmitter. This corresponds to a magnetic field strength of between 1.25× 10$^{-10}$ and 125×10$^{-10}$ Tesla (1.25 and 125 microgauss) for the transmission frequency (typically on the order 128 kHz) and corresponding wavelength used.

This magnetic field is extremely weak. The receiver system is thus sensitive to electromagnetic perturbations (noise, EMI, etc., herein also referred to as "parasitic" or "perturbing" signals) having at least a similar magnitude. For example, an electrical field having a similar frequency and an amplitude of from 40 to 4000 mV/m induces in the receiver coil signals of a magnitude similar to signals induced in the receiver coil by the useful signal emitted by the implant. Such perturbating signals are created, for example, by electrical power lines carrying domestic current (at the frequency of the network system) or by electronic apparatus such as a computer video display system (e.g., at the synch frequency of the video line sweeping).

To overcome the noise problem, several solutions have been implemented, alone and in combination.

U.S. Pat. No. 4,944,299 refers to a system of filtering which is combined with a system of encoding the information in order to reduce the risks of error due to external perturbations. The noise is said to be eliminated due to the fact that it does not contain the encoded characteristics of the expected signal. A problem with this technique is that it does not operate at the level of receiving the signal to suppress noise, but rather, after detection of the signal to remove the noise sensed.

DE 39 36 547 refers to a solution upstream of the processing of the signal, by a selective elimination of the noise collected. The device refers to two coils in which one is placed directly in proximity to the signal emitted by the implant and the other is placed remotely to the first in a manner that the second coil receives only a very weak part of signal emitted by the implant. In theory, by appropriate placement, the two coils receive essentially the same quantity or intensity of perturbating signals from the relatively distant noise source. The use of two identical coils connected in opposite polarity results in the coupled noise signals from the distant sources canceling each other by subtraction, before the induced and "summed" signals are presented to the amplifier circuitry. In this manner, according to the document, only a small part of the useful signal from a proximate (near) source is attenuated and the larger part of perturbating signals from a distant source is eliminated.

Nevertheless, this system suffers from the problem that it cannot eliminate completely a perturbating signal emitted by a source that is not effectively the same distance from the two coils (an "intermediate" source). This problem typically occurs, for example, when a video display monitor (CRT) is spaced thirty centimeters from the programmer receiving coil, which situation exists with many programmers. In such case, the difference in distance between each of the two coils and the electromagnetic interference source is not negligible, and the system will only partially eliminate the parasitic signals. Thus, although the circuit referred to in DE A 39 36 547 does adequately eliminate noise signals of a distant origin, it does not attenuate practically signals of an origin proximate to one of coils, and eliminates only partially signals having their source in an intermediate zone.

There is a continuing need for improved noise suppression in receiving telemetry signals from implants.

SUMMARY OF THE INVENTION

It is, therefore, an object of the present invention to substantially eliminate perturbating signals of distant origin as well as semi-distant origin (that is to say situated in an intermediate zone between a near field source and a distant field source), while preserving useful (desired) signals of a near origin without alteration.

Another object of the invention is to provide a system that adapts automatically, in an optimal manner, to extract the useful signal in the presence of different sources of noise, independent of the distance of the noise source to the system, and independent of their temporal dependence.

Broadly, the present invention concerns circuit apparatus and methods to extract a useful signal, emitted by an implanted active medical device, from an electromagnetic signal including a useful signal mixed with perturbing (parasitic) signals. One such device comprises:

a plurality of signal receivers disposed at different locations, each signal receiver being sensitive to the magnetic component of an electromagnetic signal, and the distance between the signal receivers being negligible relative to the wavelength of the electromagnetic signal;

a plurality of amplifiers wherein one amplifier is respectively associated with each signal receiver and each amplifier has a gain that is separately adjustable;

an adder circuit, receiving as inputs the plurality of amplifier output signals and having an output signal corresponding to a consequent sum of the amplifier inputs;

means to evaluate a representative magnitude of the level of the consequent sum signal; and calculating means for selecting the amplifier gain values to minimize the representative magnitude in a preliminary step in the absence of a useful signal, and maintaining the amplifier gains at the selected values in a subsequent step in the presence the useful signal.

Preferably, the number of signal receivers is two. The useful signal is preferably a telemetry signal emitted by the implant containing information such as data acquired by the implant (e.g., cardiac electrogram samples, pacing marker events, histogram data, holter data, etc.) or implant operating parameters (i.e., values programmed by the programmer or fixed values and data).

The representative magnitude can notably be the absolute value of the sum signal, or an efficient value of the consequent sum signal such as a root mean square.

The calculation means can be a computing device means, such as a calculator, a computer, or a logic circuit, for performing a linear calculation to solve a linear equation system, where the amplifier gain values constitute the unknowns.

The invention also is directed to a process to extract a useful signal, emitted by an implanted medical apparatus, from an electromagnetic signal comprising the useful signal mixed with perturbing (parasitic) signals. One such method includes the steps of:

(a) in a preliminary step: receiving electromagnetic signals including the parasitic signals by at least two signal receivers disposed at different locations spread apart, in the absence of any emission of the useful signal by the implanted apparatus (inhibiting such emission if necessary), each receiver being sensitive to the magnetic component of the electromagnetic signals, the distance between the receivers being negligible relative to the wavelength of the electromagnetic signals; separately amplifying each signal received by a receiver; summing the amplified signals delivered by amplifiers; evaluating the magnitude of the consequent sum signal; and selecting a gain value for each amplifier that results in a minimized magnitude of the consequent sum signal; and (b) in a subsequent step: causing (or permitting) the implanted apparatus to emit the useful signal; receiving the electromagnetic signals including the useful signal mixed with any parasitic signals by the said at least two signal receivers and; maintaining the amplifier gain values at the gain values selected during the preliminary step.

Preferably, steps (a) and (b), are alternately repeated periodically, whereby the amplifier gains are re-evaluated (and readjusted if needed) on each execution of step (a).

The step of determining or adjusting the gains of the amplifiers in step (a) is preferably performed by establishment of a linear system of P equations with P+1 unknowns, where the unknowns are the gain values, and the coupling coefficients between magnetic fields and antennae are known. The solution is obtained by fixing arbitrarily one amplifier gain value and by deducing the other P amplifier gain values according to the one fixed value. The result will produce a minimum amplitude sum signal corresponding to the sensed noise. On a subsequent reevaluation of the system of equations different amplifier gains may be arbitrarily set, or the same gain value may be arbitrarily set to a different value, with the other gains deduced relative to the newly set amplifier gain.

BRIEF DESCRIPTION OF THE DRAWING

Further features of the invention, its nature and various advantages will be more apparent from the accompanying drawing and the following detailed description of the invention, in which the FIGURE shows a block schematic diagram of the apparatus in accordance with a preferred embodiment of the invention.

DETAILED DISCUSSION OF THE INVENTION

In the case of the telemetry of information provided by an implant, useful signals as well as parasitic signals are transported in the form of magnetic fields. The total magnetic field signal $B_T$ (expressed in the form of a vector) sensed at a signal receiver (in form of a coil or bobbin) depends on the given instant t, and the location in a given space of which r is a position vector. It is the sum of the useful signal $B_s(r,t)$ and the P parasitic signals $B_i(r,t)$, as a function of space and time:

$$B_T(r,t) = B_s(r,t) + \sum_{i=1}^{P} B_i(r,t) \qquad (1)$$

If a single receiver coil is used, it will receive all fields, both the useful signal and the undesired perturbations, in the form of $B_T(r,t)$.

In accordance with the present invention, in place of a single receiver, at least two, and optionally more than two, receiver coils, operating with a particular linear combination of signals delivered by the receiver coils allow to preserve (i.e., retain) solely the component $B_s$ of the useful signal, and to eliminate effectively (i.e., suppress) the components $B_i$ of the parasitic sources.

By hypothesis, one will consider that the various receiver coils are situated at different spatial locations, and that the spectral components of significant parasitic signals, in regard of the bandwidth of the device, have a wavelength greater than the dimensions of the container enclosing the various signal receivers. Consequently, this last approximation means that, if two receiver coils are placed at two distinct points and collect the same parasitic field $B_i$, then the parasitic signals are received synchronously.

In the present application of implanted active medical devices, the wavelengths of the electromagnetic signals studied are on the order of a kilometer and distances between the two or more receiver coils are on the order the tens of centimeters. The latter spacing is due to physical limitations on the size of an external programmer. Accordingly, the foregoing assumptions in question are justified.

As a formal manner, this hypothesis allows the perturbating field $B_i$ to be separated according to the variables r and t, so that the parasitic field equation can be written as, for all i:

$$B_i(r,t) = \lambda_i(r) * \mu_i(t), \qquad (2)$$

where $\lambda_i(r)$ is a representative function of the orientation and the amplitude of the field, and $\mu_i(t)$ is a function expressing the time dependence of $B_i$.

The device of the invention, illustrated schematically on the Figure, comprises a plurality 100 of N receiver coils $A_1$ to $A_N$, that collect an induced magnetic flux and produce N voltages $V_1$ to $V_N$, that are applied to a plurality 200 of N amplifiers, respectively, each amplifier having a variable gain ($g_1$ to $g_N$).

More precisely, at the level of the jth receiver coil, the electromotive force that is created is the sum of the derivative of the magnetic flux that crosses the receiver coil, and is expressed as:

$$V_j(t) = \sum_{i=1}^{P} C_{ij} * \left[ \frac{d\mu_i(t)}{dt} \right] \qquad (3)$$

where $C_{ij}$ is a coupling constant between the field $B_i(r,t)$ and the jth coil.

If one considers an assembly of N receiver coils subjected to P parasitic fields $B_i(r,t)$, having voltages $V_j(t)$ collected on each coil, which are each amplified by an amplifier of gain $g_j$, then one can show that there exists a combination of gain values $g_j$ such that the sum of product $V_j(t)*g_j$ cancels, on the condition that N=P+1. In others terms, the set of P distinct perturbating signals can have a self annihilating effect if they are sensed with a number of receiver coils that is one more than the number of parasitic signal sources. Once this effect is obtained, the superposition of the useful field $B_s$ emitted by the implant permits its detection in an optimal manner, given that the sum of perturbating signal contributions in the field is a minimum, if not completely canceled.

To this end, gains $g_1$ to $g_N$ of the N amplifiers are individually set by control signals 501, which are generated by a calculation means 500. The control signals 501 may be a parallel data bus setting a digital code or a plurality of N signal lines for controlling each amplifier. The amplified voltages are then summed by adder circuit 300 to provide a consequent sum signal V. A processing means 400, acting on V, provides a representative magnitude |V| 401, that can be an absolute value or an efficient value such as a root mean square. The calculation means 500 then evaluates the magnitude |V| and adjusts individually the gains $g_1$–$g_N$ of the N amplifiers 200, by control signals 501, to obtain a magnitude |V| 401 that is minimal. In the case that the number P of perturbating signals is less then the number N of receiver coils, the system will operate to set the different gains $g_N$ in such manner that signal 401 magnitude |V| is null (zero).

Once the phase of canceling the perturbing signals is realized, the useful signal can be emitted by the implant to the system of receiver coils. This will result in a signal V that is non zero, and is passed to the input of a device for processing of the content of the useful signal. Such a processing device, and the useful signal and its content, form no part of the present invention, are known in the art, and, therefore, are not discussed herein.

Importantly, the non-zero signal V cannot be canceled by the system of N receiver coils. This is because the P=N−1 perturbating signals are already canceled and, to cancel also the useful signal, it would be necessary to have N+1 receiver coils. However, there are only N receiver coils, making the cancellation of the useful signal information unlikely.

A simplified realization of the present invention can be advantageously implemented in a two receiver system, having only two identical coils (N=2) and two amplifiers and a circuit for adding the two amplified voltages $V_1$ and $V_2$.

In the foregoing discussion, it is assumed that the P perturbating fields each have their own time dependence. This means that the P sources can perturb the reception of the useful signal, by separately emitting their own parasitic signals (for example, a video monitor that emits a series of parasitic peaks corresponding to line return (synchronization pulses), electrical conductors, lights and other devices that emit parasitic signals at the frequency of the sector, e.g., 50 Hz, 60 Hz, etc.).

If one approaches a source of perturbation, some of the parasitic signals are going to increase in amplitude and the system will be very sensitive to displacement. On the other hand, if one is sufficiently far from the various sources, the form of the total parasitic signal captured will depend little on the position of the system of receiver coils and will be able to be locally described by a unique field. In others words, this means that if one does not move, or moves little, as compared to the different perturbing sources, by remaining sufficiently distanced from the perturbing sources, the perturbing sources are not localized and the parasitic signals will be received as if they came from a single source of perturbations. Therefore, the parasitic signals will appear to the receiver coils as if P=1, regardless of the actual number P of different perturbing sources). Consequently, two receiver coils are sufficient to cancel such a "single" perturbating field.

The following describes a manner of implementing the system of the invention in a simplified system having only two receiver coils. The generalization of the two coil case to a system having a larger number of receiver coils is believed to be immediately apparent to a person of ordinary skill.

During a first phase of functioning of the device, an ambient noise measure is realized in the absence of the useful signal. The calculator means 500 adjusts the values of gains $g_1$ and $g_2$ of the two amplifiers in a manner to minimize the value of |V|. In this example, one assumes that the perturbating field is assimilated to a unique field $B_1(r,t)$.

Nevertheless, following the placement of the receiver coils as compared to the source $B_1$, voltages $V_1$ and $V_2$ cannot be equal, and the individual gain adjustment $g_1$ and $g_2$ allows to cancel the non symmetrical effects of the field $B_1$ on each of the coils.

Once this preliminary adjustment has been undertaken, e.g., by selecting $g_1$ and adjusting $g_2$, the useful signal $B_s$ is then emitted in a subsequent phase by the implanted device, and received by the system of two coils. The corresponding resultant signal value V, now deprived of the effects of noise, then can be sent at output 301 to a circuit to process the useful signal (not shown). By advantageously performing an alternating sequence of a first phase of receiving of the noise (a phase where the implant is silent ($B_s$=0) and a phase of emission of the $B_s$ signal (in the presence of noise)), the system is capable of automatically adapting even to variations of effects of the perturbating signals on the receiver coils caused by displacement of the receiver coil portion of the programmer or, possibly, of the source of the noise.

It should be understood that this invention can be implemented using conventional electronic circuits and using circuits together with microprocessor based processing of signals under appropriate software control. In particular, the calculator 500 can advantageously be constituted as a calculation module capable of solving a system of N linear equations which corresponds to the noise cancellation by the sum of product $V_j(t)*g_j$, for all j ∈ [1, N]; wherein one of the N gains $g_N$ will be arbitrarily fixed and all of the other gains will be selected relative to the one fixed gain. A representative technique for solving such a linear equation system is found in C. Cagnac, E. et al., Traité de mathématiques spéciales, Vol. I (Algèbre), chapter XV-2 (Systèmes de Kramer), pages 123 et seq., édition Masson, 1970. Alternatively, the calculation module could be implemented in a hardwired circuit to solve the equation set, or which interactively adjusts selected gain values and tests the result and sum signal until a minimum is identified.

One skilled in the art will appreciate that the present invention may be practiced by other than the foregoing embodiments, which are presented for purposes of illustration and not of limitation.

We claim:

1. A device to extract a useful signal, emitted by an implanted medical apparatus, in an electromagnetic signal having a wavelength and including the useful signal mixed with a parasitic signal, comprising:

a plurality of signal receivers located at distinct points and spaced apart relative to each other by a distance of separation, the distance of separation between said signal receivers being negligible relative to the wavelength of the electromagnetic signal, each signal receiver being sensitive to the magnetic component of the electromagnetic signal;

a plurality of amplifiers, each one of said plurality of amplifiers being coupled to one of the plurality of signal receivers and having an input, an adjustable gain, and an amplified output;

means for summing the amplified outputs and providing a consequent sum signal output;

means for evaluating a magnitude representative of the level of the consequent summed signal, and means for processing said magnitude and adjusting the gains of said plurality of amplifiers to minimize the magnitude in a preliminary step in the absence of the useful signal, and to maintain said amplifiers at said adjusted gains in a second step in the presence of the useful signal.

2. The device of claim 1, in which the plurality of signal receivers comprises a first signal receiver and a second signal receiver.

3. The device of claim 1, wherein the processing means provides the representative magnitude as one of an absolute value of the consequent sum signal and an efficient value of the consequent sum signal.

4. The device of claim 1, in which the processing means further comprises a linear calculation means for solving a system of linear equations, each equation in the system having an unknown, in which said amplifier gains are the unknowns.

5. A process to extract a useful signal, emitted by an implanted medical apparatus, in an electromagnetic signal having a wavelength including the useful signal mixed with a parasitic signal, including the steps of:

a) conducting a preliminary step of:
      (i) inhibiting the emission of the useful signal by the implanted apparatus;
      (ii) receiving the parasitic signal by a plurality of signal receivers located at different positions and spaced a distance apart relative to each other, each signal receiver including an associated amplifier having an adjustable gain and an amplified output and being sensitive to the magnetic component of the electromagnetic signal, the distance separating the signal receivers being negligible as compared to the wavelength of the electromagnetic signal;
      (iii) summing the amplified outputs delivered by the amplifiers and providing a sum signal output;
      (iv) evaluating the magnitude of the sum signal; and
      (v) adjusting the gain of each amplifier to the extent necessary to provide a minimum sum signal; and b) conducting a subsequent step of:
      (i) causing the implanted device to emit the useful signal,
      (ii) collecting at the plurality of signal receivers the electromagnetic signal including the useful signal and the parasitic signal, and
      (iii) maintaining the values of the gains of the amplifiers at the values adjusted in the preliminary step (a) (v).

6. The process of claim 5, further comprising repeating steps (a) and (b) sequentially so that the gains of amplifiers are re-evaluated and readjusted, if necessary, on each execution of step (a).

7. The process of claim 5, in which the step of adjusting the gain in step (a) (v) comprises:

establishing a linear system of P equations including P+1 unknowns, wherein the unknowns are said amplifier gains, and the coefficients are the coefficients of coupling between fields and antennae;

fixing arbitrarily the value of one gain; and deducing the P other values of gain relative to the fixed gain.

8. The method of claim 7 further comprising repeating steps (a) and (b) sequentially so that the gains of the amplifiers are re-evaluated and readjusted on each execution of step (a).

9. The method of claim 8 wherein on each repetition of step (a), the amplifier gain value arbitrarily selected is of a different amplifier than the amplifier selected on the preceding execution of step (a), and the other amplifier gain values are deduced relative to said one arbitrarily selected gain value.

10. The method of claim 8 wherein on each repetition of step (a), the amplifier gain value arbitrarily selected is a different gain value than the gain value selected on the preceding execution of step (a), and the other amplifier gain values are deduced relative to said one arbitrarily selected gain value.

11. An apparatus for separating a useful signal emitted by an implanted active medical device from an electromagnetic signal having a wavelength and including the useful signal and perturbing signals, comprising:

a first plurality of signal receivers, said signal receivers being spaced apart relative to each other a distance that is negligible with respect to the electromagnetic signal wavelength, each receiver having a coil sensing a magnetic field component of the electromagnetic field and an output signal corresponding to the sensed magnetic field component;

a second plurality of amplifiers associated with said first plurality of signal receivers so that each signal receiver is coupled to an amplifier, each amplifier having an input receiving a coil output signal, an adjustable gain, and an amplified output;

an adder circuit summing the amplified outputs of said second plurality of amplifiers and having a sum signal output;

means for processing said sum signal and controlling the plurality of amplifier gains in one of a first operating mode in the absence of said useful signal, to select the gains of said plurality of amplifiers to minimize the magnitude of said sum signal, and a second operating mode in the presence of said useful signal, to maintain the amplifier gains as selected in said first operating mode, thereby to obtain a sum signal representative of the useful signal in the second operating mode.

12. The apparatus of claim 11 wherein the first plurality of receiver signal coils further comprise a first coil and a second coil, and wherein the second plurality of amplifiers further comprises a first amplifier and a second amplifier, the first and second amplifiers being connected to amplify the first and second coil output signals, respectively.

13. The apparatus of claim 11 wherein said processing means in said first operating mode further comprises:

means for receiving said sum signal and providing a second signal representative of the sum signal; and first means for selecting arbitrarily a first value of one of said plurality of amplifier gains and second means for selecting a value of each of the other of said plurality of amplifier gains to minimize the second signal.

14. The apparatus of claim 13 wherein the second signal comprises one of an absolute value of the sum signal and an efficient value of the sum signal.

15. The apparatus of claim 14 wherein the second selecting means operates to select one of said other amplifier gain values at a time in a predetermined sequence.

16. The apparatus of claim 13 wherein the first and second selecting means further comprise a set of linear equations in which the amplifier gain values are the unknowns, and a calculation module processing said equation set to solve the unknowns.

17. An apparatus for receiving useful telemetry signals emitted at a first wavelength by an implanted active medical device in the presence of perturbing noise, comprising:

a first receiver coil having a first coil output signal that is responsive to the magnetic field component of an electromagnetic signal at said first wavelength;

a first amplifier having an input coupled to the first coil output signal, an adjustable gain, and an amplified output;

a second receiver coil having a second coil output signal that is responsive to the magnetic field component of said electromagnetic signal at said first wavelength;

a second amplifier having an input coupled to the second coil output signal, an adjustable gain, and an amplified output;

an adder circuit having as inputs said first and second amplifier outputs and having an output corresponding to the sum of the first and second amplifier outputs;

a circuit having an input receiving the adder circuit output and an output signal that is a magnitude representative of the magnitude of the adder circuit output; and means for processing said magnitude in a first operation in the absence of the useful telemetry signal to adjust the gains of the first and second amplifiers to first and second gain values, respectively, to minimize the magnitude, and in a second operation in the presence of the useful telemetry signal to acquire the useful telemetry signal based on said adjusted first and second amplifier gains suppressing said perturbing noise.

18. The apparatus of claim 17 wherein said processing means first operation further comprises first means for selecting arbitrarily one of said first and second gain values, and second means for selecting the other of the first and second gain values to minimize the magnitude.

19. The apparatus of claim 18 wherein the circuit output signal magnitude further comprises one of an absolute value of the sum signal and an efficient value of the sum signal.

20. The apparatus of claim 19 wherein the first and second selecting means further comprise a set of linear equations in which the amplifier gain values are the unknowns, and a calculation module processing said equation set to solve the unknowns.

21. The apparatus of claim 20 wherein the calculation module comprises a microprocessor.

* * * * *